United States Patent [19]

Galbraith

[11] 4,300,310

[45] Nov. 17, 1981

[54] IDENTIFICATION AND SORTING OF PLANT HETEROKARYONS

[75] Inventor: David W. Galbraith, Lincoln, Nebr.

[73] Assignee: The Board of Regents of the University of Nebraska, Lincoln, Nebr.

[21] Appl. No.: 172,979

[22] Filed: Jul. 28, 1980

[51] Int. Cl.$^3$ .............................................. A01H 1/02
[52] U.S. Cl. ....................................................... 47/58
[58] Field of Search .......................................... 47/58

[56] References Cited

U.S. PATENT DOCUMENTS 3,832,801  9/1974  Carlson et al. ......................... 47/58

OTHER PUBLICATIONS

Plant Cell, Tissue, and Organ Culture, Reinert et al., 1977, Springer-Verlag, N.Y., pp. 467–505.

Primary Examiner—Robert E. Bagwill
Attorney, Agent, or Firm—Vincent L. Carney

[57] ABSTRACT

To label heterokaryons formed by fusion of different somatic tissue cells, somatic tissue cells from one plant are immersed in a first solution including polysaccharidase and fluorescein isothiocyanate and somatic tissue cells from a different plant are immersed in a second solution including polysaccharidase and rhodamine isothiocyanate for a period of from 12 to 18 hours, after which protoplasts emerge, with those from one plant fluorescing green-yellow and those from the other fluorescing orange-red. The protoplasts are then fused in a polyethylene glycol solution. The heterokaryons are identified and sorted by a commercial cell sorter which relies upon the fluorescence from both markers.

17 Claims, No Drawings

IDENTIFICATION AND SORTING OF PLANT HETEROKARYONS

BACKGROUND OF THE INVENTION

This invention relates to parasexual hybridization.

In parasexual hybridization, protoplasts of higher plant cells are fused and some heterokaryons form a callus mass which under some circumstances differentiates into apparently normal, fertile, new plants. This procedure is disclosed by Carlson, P.S. et al; Proc. Natl. Acad. Sci., 69, 2292-2294 (1972).

In one technique of parasexual hybridization, somatic cells of different plants are treated in suitable osmotica containing high concentrations of commercial polysaccharidase preparations until their cell walls have become degraded and the protoplasts emerge. Such techniques have been described by Bajaj, Y.P.S. in Applied and Fundamental Aspects of Plant Cell, Tissue and Organ Culture, pp 467-577, Springer-Verlag (1977).

After the protoplasts emerge, they are subjected to conditions that cause some pairs to fuse and form heterokaryons. Several nonspecific chemical treatments induce homologous and heterologous fusion, even to the extent of the creation of inter-kingdom hybrids. The most popular nonspecific chemical fusogen is polyethylene glycol as described by Kao, K.N., Molec. Gen., Genet. 150, 225-230 (1977).

Some of the heterokaryons initiate cell wall deposition and cell division and may develop into normal plants. Techniques for such regeneration are discussed in Applied and Fundamental Aspects of Plant Cell, Tissue and Organ Culture, pp 467-577, Reinert, J., Bajaj, Y.P.S. ed. Springer-Verlag (1977). Specific selection schemes allow the isolation of interspecific hybrid callus for such regeneration.

In the prior art techniques of hybrid parasexual hybridization, several different techniques are used for the identification and selection of true binucleate heterokaryons from fused and unfused parental protoplasts, but at present, no general prior art methodologies are available that can achieve this identification and selection in a satisfactory manner.

Some of the prior art methods which are most significant are those which rely upon: (1) separation in accordance with the known different growth requirements of the callus tissue; (2) differential sensitivities of parental tissue to drugs and metabolic inhibitors; (3) microscopical examination of cytological markers during fusion and cultivation of protoplasts; (4) complementation of auxotrophic parental tissue following protoplast fusion and culture in a minimal medium; and (5) density gradient centrifugation to separate parental protoplasts of differing buoyant densities from hybrid protoplasts of intermediate density.

None of the above techniques have been entirely satisfactory. Each of them has had certain disadvantages such as: (1) it is difficult to predict the characteristic of the somatic hybrid upon which selection is to be based such as the growth requirements, differential sensitivities to drugs and metabolic inhibitors or the like; (2) suitable parental tissue is not available with characteristics that complement to form a characteristic suitable for selection such as susceptibility to drugs, susceptibility to light, weight differences, or natural differentiation characteristics to serve as markers or the like; and (3) certain of the techniques put too much strain on the cells.

Fluorescent labeling has been used in the prior art for the identification and sorting of cells. It has been used sucessfully in the sorting of animal cells by formation of antibodies to the animal cells and attachment of the label to the antibody for later attachment to cells.

The growing of higher plant cells in culture and the labelling of such cells by fluorescence marking was reported by D. W. Galbraith and J. E. C. Galbraith, Überreicht vom Verfasser Nicht einzeln im Buchhandel: Sonderdruck aus Zeitschrift fur Pflanzenphysiologie, Band 93, Heft 2, Seite 149-158 (1979) Gustav Fischer Verlag Stuttgart, West Germany. In the experiments on which that report is based, an attempt was made to mark freshly isolated protoplasts as well as suspension cultured cells but failed with respect to the freshly isolated protoplasts.

SUMMARY OF THE INVENTION

It is an object of this invention to provide a novel method for labelling plant protoplasts derived from somatic tissue.

It is a further object of this invention to provide a novel method for parasexual hybridization.

It is a still further object of this invention to provide a novel method for the identification and sorting of heterokaryons from somatic plant tissue.

In accordance with the above and further objects of the invention, somatic cells from different plants are obtained, the cells being of the type which regenerate to produce new fertile plants. The cells from one plant are immersed in a medium that causes its protoplasts to emerge and which contains a cell marker. The cells of the other plant are also immersed in a medium that causes its protoplasts to emerge and which contains a cell marker but the marker is different from the cell marker used for cells of the one plant. Surprisingly, it has been found that protoplasts are adequately marked in this process so that after fusion heterokaryons can be identified and sorted.

After the protoplasts have emerged from the different groups of cells, with each group of cells marked differently, they are fused and the heterokaryons are separated by identifying those which have the two different markers. The separated heterokaryons are regenerated to produce new fertile plants.

As can be understood from the above description, the method of this invention has the advantages of enabling the ready identification by cell sorters and the like of plant heterokaryons which may be used to regenerate new plants.

DESCRIPTION OF THE PREFERRED EMBODIMENT

Broadly, the invention contemplates the distinctive marking of protoplasts from somatic tissue taken directly from intact plant organs of different plants while the protoplasts are being isolated and the induced fusion of the protoplasts while distinctly marked so that heterokaryons can be identified by the combinations of the two or more distinctive markers. This identification can be done automatically by commercial cell sorters to provide ready sorting.

More specifically, mesophyll tissue from two different plants are prepared and immersed in different enzyme baths to remove their cell wall and cause emergence of the protoplasts. The two baths each have a different color fluorescent marker inserted at the same time as the enzyme is causing the emergence of the protoplasts. The incubation is for a relatively long time such as between 18 and 24 hours to permit adequate marking of the protoplasts.

The distinctly marked protoplasts are separated and fusion is induced by standard techniques. The heterokaryons now are marked with two different fluorescent colors and can be separated by standard cell sorters in accordance with the two fluorescent colors. For example, sorters interrogate a stream of electrically-charged cells with a laser beam to detect those that have two colors and deflect the ones having two colors electrostatically into separate containers.

The time required in the enzyme of the protoplasts to emerge and be marked differs from cell type to cell type and from technique to technique for marking or for causing the protoplast to emerge. The temperature of the medium, concentration of its components and amount of agitation are also factors.

Generally, duration of time in the enzyme, the concentrations, temperature, pH and agitation for a particular cell type are limited by the obvious requirement that the marking and isolation of protoplasts must not impose conditions that kill too large a portion of the cells.

These limits on chemical conditions are also altered by a procedure in which the components of the isolating medium are added at different times. For example, the marker may be mixed with the other components after or before treatment of the cells by the other components has started. Moreover, if addition of components is separated in time, different concentrations, temperatures, pH's and degrees of agitation may be used before mixing than after mixing. These differences permit the use of toxic ingredients for a shorter time and permit some marking or isolation to take place under more favorable chemical conditions.

The lower limits on time are generally determined by the effectiveness of the marker and isolation technique in accomplishing marking and isolation of the protoplasts. These limits are also affected by temperature, concentration, pH and agitation. Moreover, in the case of timed mixing of the ingredients, the optimum conditions may be selected for certain of the components for part of the time of use.

In the preferred embodiment, plant leaves are sterilized such as by immersion in ethanol, bleach or other agent. The sterilant is removed and leaf tissue peeled or slices are obtained to provide mesophyll cells.

Low concentration of fluorescent markers are obtained. Suitable fluorescent markers are fluorescein isothiocyanate (FITC) and rhodamine isothiocyanate (RITC) or their analogs, tetramethylrhodamine isothiocyanate (TRITC) and a substituted derivative. Such materials are available commercially such as from Research Organics in Cleveland, Ohio. Other types of markers are known, and it is only important to use markers which do not affect the growth characteristics of the cell and which remain during the isolation and fusion of the protoplasts and during the selection of the heterokaryons.

The selected tissues or tissue cultures are incubated in suitable osmotica containing concentrations of commercial polysaccharidase preparations. The incubation occurs between 18 to 21 hours and at a temperature between 10 degrees and 30 degrees centigrade. The fluorescein isothiocyanate or other marker with one color is inserted during incubation in one batch of mesophyll tissue and another marker such as rhodamine is inserted during incubation in another batch of mesophyll tissue from another plant. Thus, at least two different protoplasts from different plants are marked with different colors for combination. Obviously, more than two types of cells can be used from a larger number of plants but this complicates the procedure and generally reduces its chances of success in obtaining a useful hybrid.

The type of marker should be nonspecific and thus not depend on the genetic characteristics of the protoplasts or the heterokaryons. There are many such general markers known in the art. They must attach to a portion of the protoplast without losing their distinguishing characteristic or in a manner that creates a distinguishing characteristic.

To separate the protoplasts from undigested leaf tissue, they are filtered through 8 layers of cheesecloth and pelleted by centrifugation at 50 gravities for 3 minutes. To remove small cell debris, the protoplasts are resuspended in 5 milliliters of a 25% sucrose solution. The suspension is overlayed with 5 milliliters of the appropriate osmoticum and centrifuged at 50 gravities for 3 minutes. Intact protoplasts free of cell debris are recovered from the gradient interface and pelleted following dilution with osmoticum and centrifugation at 50 gravities on the average for 3 minutes. Other techniques for separation are also known in the art.

To fuse the protoplasts, they are mixed in polyethylene glycol (PEG) which is thereafter diluted by high pH calcium solutions in a manner known in the art. In the preferred embodiment, the calcium-PEG solution includes 45 g PEG 1500, 9 mg $KH_2PO_4$, 155 mg $CaCl_2.2H_2O$ and 100 ml $H_2O$.

Although use of polyethylene glycol solution for fusion is used in the preferred embodiment, many other chemical treatments are known. They are nonspecific and induce both homologous and heterologous fusion. Some of these techniques are described by Davey, M. R. et al; Protoplasma 96, 157–172 (1978). The specific technique used is described by Kao, K. N. and Michayluk, M. R.; Planta 115, 355–367 (1974).

After fusing, the protoplast initiates cell wall deposition and cell division. During this processs, selection of heterologous fused protoplasts from the population of parental protoplasts in the third embodiment is done by a cell sorter or by a micromanipulator after observation and location through a fluorescent microscope.

Cell sorters are commercially available such as from Becton-Dickinson and are sold under the name Becton-Dickinson Fluorescence Activated Cell Sorters. One such instrument is designated as FACS IV and is sold by Becton-Dickinson FACS Systems, 500 Clyde Avenue, Mountain View, Calif. 94043. Another similar machine is sold by Coulter Electronics Inc., Hialeah, Fla. 33010.

This cell sorter permits four parameter sorting including two different fluorescent colors and two size determinations. Consequently, a distinction may be made between small and large protoplasts, between dimly and highly fluorescent protoplast and between those having been marked both by fluorescein and rhodamine fluorescence and those marked with only one of the two markers. It has the ability to sort at rates of up to 5,000 cells per second and does not affect cell viability nor introduce contamination.

Cells to be sorted are contained in a reservoir and are passed through an orifice of defined aperture in this instrument. The orifice is constrained to vibrate ultrasonically by a piezoelectric crystal and the vibration causes the fluid flow containing the cells to break into small precisely defined droplets each containing at maximum one cell.

Prior to the formation of the droplets, the fluid flow is interrogated by a laser beam. The degree of light scattering, which is a measure of cell size, is recorded electronically. The degree of fluorescence that is produced by the cell is also recorded using specific filters and further multipliers.

The machine can be operated in two complementary modes. In the first, cell populations are analyzed for the various parameters of cell size and of fluorescence. This information is stored and can be displayed and recorded as histograms.

In the second mode of operation, cell-sorting, the parameters of cell size and fluorescence are used to program the selection of subpopulations of the original cell sample. For sorting, the orifice is maintained at a small potential so that each droplet, when formed, possesses a small surface charge. Based on the information obtained by prior laser interrogation of the cell, the cell sorter applies an electrical field across plates parallel to the path of the falling droplets. The intensity and polarity of the field determines the path of the droplets into one of three collection vessels. Subpopulations can be selected on the basis of any one, or combination of four, distinct parameters. The population thus selected is highly homogeneous.

The technique of selection by micromanipulator is described by Kao (supra) using an ordinary visible light bright field microscope. This technique can be used identically using a fluorescent microscope to select the heterokaryons by the two different colors. Standard techniques are known for such observation and selection based on two colors and automatic systems are available.

The heterokaryons may develop into fertile plants in a growth medium. The callus subsequently is induced to produce roots and shoots by adjusting hormone levels in growth medium (IAA, BA) or it can be grafted directly onto parental stock. The procedure for growth has been described in the above mentioned publication of Kao (1977). Generally, it requires the suspension of the protoplasts in dishes of culture medium. Root and shoot initiation can be induced after 4 or 5 weeks of culturing such medium in a manner known in the art.

The technique of parasexual hybridization is general and can be applied generally to plant cells. For example, seeds of *Nicotiana tabacum* of *Nicotiana glutinosa* and of *Nicotiana langsdorffii* and *Nicotiana glauca* are germinated and cultivated under standard greenhouse conditions. Fully expanded leaves closest to the plant apex having an approximate surface area of 6,000 square millimeters are selected.

The plant leaves are sterilized by sequential immersion in 70% ethanol for 5 seconds and in a 33% solution of commercial bleach for 15 minutes. Residual sterilant is removed by two 5-minute washes in sterile distilled water. The sterile leaves are preplasmolysed in sterile osmoticum in accordance with the methods described by Chupeau et al: Molec. Gen. Genet., 165, 239-245 (1978). The osmoticum is described on page 240 and is hereinafter referred to as To. For *Nicotiana tabacum* and *glutinosa* a modification of To osmoticum, referred to as NTTo, contains 5% supplemental mannitol.

The leaf fragments of *Nicotiana glauca*, following removal of the lower epidermis, and slices of *Nicotiana langsdorffii*, *Nicotiana tabacum* and *Nicotiana glutinosa* are incubated in 10 mililiter aliquots of sterile enzyme solution in the dark for between 18 and 21 hours at 25 degrees centigrade with gentle reciprocal shaking (30 excursions per minute). The enzyme solutions are those described by Chupeau et al (1978) cited above.

The protoplasts are separated from undigested leaf tissue by filtration through 8 layers of cheesecloth and are pelleted by centrifugation at 50 gravities (average) for 3 minutes. The pellets of protoplasts of *Nicotiana glauca*, and of *Nicotiana tabacum* or *Nicotiana glutinosa* are gently suspended in a 5 to 10 milliliter solution containing, respectively, 20 or 25 percent weight to volume of sucrose in the medium described by Chupeau et al cited above. The protoplast suspension is overlayed with 5 milliliters of the appropriate osmoticum (To or NTTo) and is centrifuged at 50 gravities (average) for 3 minutes. Intact protoplasts free of all cell debris are recovered from the gradient interface and are pelleted following dilution with osmoticum by centrifugation at 50 gravities for 3 minutes.

The protoplasts are separately labelled with fluorescein isothiocyanate (FITC) or with rhodamine isothiocyanate (RITC) or tetramethylrhodamine isothiocyanate by the addition of 25 milliliters of 5 milligrams per milliliter ethanol solution of the appropriate reagent immediately following the addition of the leaf fragments to 10 milliliters of the enzyme solution. The process of simultaneous protoplast production and labelling is carried out over 18 or 21 hours at 25 degrees centigrade in darkness. Labelled protoplasts are purified as described for unlabelled protoplasts.

Protoplast fusion is induced according to the general procedures of Kao et al referred to above. The crude or purified protoplasts are mixed to give an approximately equal proportion of separately labelled fluorescent populations at a concentration of 1 to 1.5 times $10^5$ per milliliter To or NTTo as appropriate. Aliquots (10 microliters) are transferred to separate petri dishes. The protoplasts in the droplets are allowed to settle into the plastic surface for 10 minutes.

Fusion is initiated by the addition of 20 microliters of polyethylene glycol solution. The composition of the polyethylene glycol is 45 grams of polyethylene glycol of 1500 molecular weight, 9 milligrams of $KH_2PO_4$, 155 milligrams of $CaCl_2.2H_2O$ and 100 milliliters of water. It has a pH of 6.5.

After 15 minutes, the polyethylene glycol solution is eluted with 50 microliters of elution medium. The elution medium typically added to the polyethylene glycol composition above contains 0.4 molar mannitol and 50 millimolar calcium chloride with 50 millimolar of glycine at a pH of 10.5. In the alternative of 0.24 M Ca($NO_3$)$_2$ and 50 millimolar of glycine or 0.3 molar of calcium chloride can be used.

After a further 15 minutes the protoplasts containing the droplets are washed by sequential removal and 50 microliter aliquots of culture medium are added. The protoplasts are then washed with a total of 500 microliters of culture medium in 50 microliter aliquots at 5-minute intervals.

The protoplast culture and plant regeneration media are based on the publication of Kao (supra) cited above. The *Nicotiana glauca* and *Nicotiana langsdorffii* protoplasts are resuspended in small Falcon petri dishes in 5 milliliters culture medium at a concentration of $10^3$ to $10^5$ protoplasts per milliliter. Protoplasts of *Nicotiana tabacum* and *Nicotiana glutinosa* are resuspended to the same population density in the culture medium supplemented with 4 percent mannitol. The heterokaryons are selected by either method described above. The selected heterokaryons are cultured in darkness or under low intensity fluorescent lighting of approximately 300 lux.

After 4 to 5 weeks of culture in the media, all clusters are transferred into 1 milliliter aliquots of solidified agar media prepared in Falcon petri dishes. Shoot initiation and leaf production are induced by medium solution including mineral salts, sugars, organic acid, casamino acid, vitamins, all ingredients at same levels as described by Kao (supra), except plant hormones are omitted and replaced by 0.5 mg/L of indole-3-acetic acid (IAA), 1 mg/L of 6 benzyladenine (6BA), and 2 percent glucose. Shoot production and leaf production are induced by this medium under low light conditions at about 300 lux for periods of 16 hour light with interspersed 8 hour periods of darkness.

After a further 6 to 8 weeks, root initiation is achieved by transfer of the leafy callus pieces onto a medium containing mineral salts, sugars, organic acids, vitamins, casamino acid and 2 percent glucose. Following the appearance of roots, plantlets are transferred into vermiculite for further growth under greenhouse conditions.

As can be understood from the above description, the method of this invention has several advantages in that it permits ready nonspecific labelling, identification and sorting heterokaryons. Thus, it provides a technique which prevents the hetrokaryons from being overgrown by a more populous parent tissue.

Although a preferred embodiment of the invention has been described in some detail, many variations in the invention are possible within the light of the above teachings. It is therefore to be understood that, within the scope of the appended claims, the invention may be practiced other than as specifically described.

What is claimed is:

1. A method of parasexual hybridization of plants comprising the steps of:
   removing the cell wall from and marking a first group of cells that are able to regenerate and are taken directly from intact plant organs to release marked protoplasts;
   said step of removing the cell wall from cells and marking a first group of cells comprising the step of removing the cell wall from the cells and marking the protoplasts in steps which occur at least in part concurrently;
   removing the cell wall from and marking a second group of cells that are able to regenerate to release marked protoplasts;
   the step of removing the cell wall from and marking a second group of cells comprising the step of removing the cell wall from the cells and marking the protoplasts in steps that are performed at least in part concurrently;
   fusing the marked protoplasts from said first group of cells with the marked protoplasts from said second group of cells; and
   identifying heterokaryons from said markings.

2. A method of claim 1 in which the step of identifying heterokaryons includes the step of indicating the number of heterokaryons.

3. A method according to claim 2 in which the step of identifying heterokaryons includes the step of sorting the heterokaryons from other cells and cell debris.

4. A method according to claim 3 in which the steps of removing the cell wall from and marking a first group of cells and the step of removing the cell wall from and marking a second group of cells each include the steps of incubating said cells in polysaccharidase for a period of time sufficiently long for the marker to attach to protoplast and sufficiently short to provide at least one viable sorted marked heterokaryon.

5. A method according to claim 4 in which the step of removing the cell wall from and marking protoplasts from a first group of cells includes the step of removing the cell wall from and marking protoplasts with a fluorescent marker.

6. A method according to claim 5 in which the step of sorting heterokaryons includes the step of sorting heterokaryons with a cell sorter.

7. A method according to claim 6 in which the step of forming and marking protoplasts from one group of plant cells includes the step of immersing mesophyll tissue from said one plant in a mixture of enzyme and a fluorescent marker.

8. A method according to claim 1 in which the step of identifying heterokaryons includes the step of sorting the heterokaryons from other cells and cell debris.

9. A method according to claim 8 in which the steps of removing the cell wall from and marking a first group of cells and the step of removing the cell wall from and marking a second group of cells each include the steps of incubating said cells in polysaccharidase for a period of time sufficiently long for the marker to attach to protoplast and sufficiently short to provide at least one viable sorted marked heterokaryon.

10. A method according to claim 9 in which the step of removing the cell wall from and marking protoplasts from a first group of cells includes the step of removing the cell wall from and marking protoplasts with a fluorescent marker.

11. A method according to claim 10 in which the step of sorting heterokaryons includes the step of sorting heterokaryons with a cell sorter.

12. A method according to claim 1 in which the steps of removing the cell wall from and marking a first group of cells and the step of removing the cell wall from and marking a second group of cells each include the steps of incubating said cells in polysaccharidase for a period of time sufficiently long for the marker to attach to protoplast and sufficiently short to provide at least one viable sorted marked heterokaryon.

13. A method according to claim 12 in which the step of removing the cell wall from and marking protoplasts from a first group of cells includes the step of removing the cell wall from and marking protoplasts with a fluorescent marker.

14. A method according to claim 13 in which the step of sorting heterokaryons includes the step of sorting heterokaryons with a cell sorter.

15. A method according to claim 1 in which the step of removing the cell wall from and marking protoplasts from a first group of cells includes the step of removing the cell wall from and marking protoplasts with a fluorescent marker.

16. A method according to claim 15 in which the step of sorting heterokaryons includes the step of sorting heterokaryons with a cell sorter.

17. A method according to claim 1 in which the step of sorting heterokaryons includes the step of sorting heterokaryons with a cell sorter.

* * * * *

UNITED STATES PATENT AND TRADEMARK OFFICE
CERTIFICATE OF CORRECTION

PATENT NO. : 4,300,310
DATED : November 17, 1981
INVENTOR(S) : David W. Galbraith It is certified that error appears in the above—identified patent and that said Letters Patent is hereby corrected as shown below:

Column 4, line 60, "protoplast" should read -- protoplasts --.
Column 6, line 25, after "isothiocyanate", add --(TRITC)--.
Column 7, line 30, after "sorting", add --of--.

Signed and Sealed this

Twenty-second Day of June 1982

[SEAL]

Attest:

Attesting Officer

GERALD J. MOSSINGHOFF
Commissioner of Patents and Trademarks